(12) United States Patent
Rubin et al.

(10) Patent No.: US 6,649,183 B2
(45) Date of Patent: Nov. 18, 2003

(54) METHODS FOR TREATING APNEA AND APNEA DISORDERS USING OPTICALLY PURE R(+) ONDANSETRON

(75) Inventors: Paul D. Rubin, Sudbury, MA (US); Timothy J. Barberich, Concord, MA (US)

(73) Assignee: Sepracor Inc., Marlborough, MA (US)

( * ) Notice: Subject to any disclaimer, the term of this patent is extended or adjusted under 35 U.S.C. 154(b) by 20 days.

(21) Appl. No.: 09/985,099

(22) Filed: Nov. 1, 2001

(65) Prior Publication Data

US 2002/0051815 A1 May 2, 2002

Related U.S. Application Data

(63) Continuation of application No. 09/515,407, filed on Feb. 29, 2000.
(60) Provisional application No. 60/122,274, filed on Mar. 1, 1999.

(51) Int. Cl.$^7$ .......................... A61F 13/00; A61K 9/48; A61K 9/64; A61K 9/20; A61K 31/445
(52) U.S. Cl. .................. 424/422; 424/434; 424/451; 424/456; 424/464; 424/45; 514/327
(58) Field of Search .................. 424/464, 465, 424/422, 434, 451, 456, 45; 514/327

(56) References Cited

U.S. PATENT DOCUMENTS

| | | |
|---|---|---|
| 3,536,809 A | 10/1970 | Applezweig ............... 424/28 |
| 3,598,123 A | 8/1971 | Zaffaroni ............... 128/268 |
| 3,845,770 A | 11/1974 | Theeuwes et al. .......... 128/260 |
| 3,916,899 A | 11/1975 | Theeuwes et al. .......... 128/260 |
| 3,961,073 A | 6/1976 | Snyder ................. 424/325 |
| 4,008,719 A | 2/1977 | Theeuwes et al. .......... 128/260 |
| 4,598,084 A | 7/1986 | Strolin-Benedetti et al. ............... 514/374 |
| 4,695,578 A | 9/1987 | Coates et al. ............ 514/397 |
| 4,753,789 A | 6/1988 | Tyers et al. .............. 424/10 |
| 4,764,515 A | 8/1988 | Borsa et al. ............. 514/255 |
| 4,835,173 A | 5/1989 | Tyers .................... 514/397 |
| 4,845,115 A | 7/1989 | Tyers .................... 514/397 |
| 4,851,407 A | 7/1989 | Wootton et al. ........... 514/213 |
| 4,929,632 A | 5/1990 | Tyers et al. ............. 514/397 |
| 5,059,595 A | 10/1991 | Le Grazie ................ 424/468 |
| 5,073,543 A | 12/1991 | Marshall et al. ........... 514/21 |
| 5,075,290 A | 12/1991 | Findley et al. ............ 514/46 |
| 5,098,909 A | 3/1992 | Williams ................. 514/286 |
| 5,120,548 A | 6/1992 | McClelland et al. ......... 424/473 |
| 5,198,447 A | 3/1993 | Tyers .................... 514/304 |
| 5,354,556 A | 10/1994 | Sparks et al. ............. 424/419 |
| 5,356,934 A | 10/1994 | Robertson et al. .......... 514/649 |
| 5,407,953 A | 4/1995 | Morgan .................. 514/397 |
| 5,422,374 A | 6/1995 | Miyao et al. ............. 514/690 |
| 5,445,604 A | 8/1995 | Lang ...................... 602/47 |
| 5,502,067 A | 3/1996 | Morgan .................. 514/397 |
| 5,519,044 A | 5/1996 | Imperato et al. ........... 514/397 |
| 5,561,149 A | 10/1996 | Azria et al. .............. 514/397 |
| 5,591,767 A | 1/1997 | Mohr et al. .............. 514/413 |
| 5,639,476 A | 6/1997 | Oshlack et al. ............ 424/468 |
| 5,674,533 A | 10/1997 | Santus et al. ............. 424/493 |
| 5,712,302 A * | 1/1998 | Young ................... 514/397 |
| 5,733,566 A | 3/1998 | Lewis ................... 424/426 |
| 6,048,879 A * | 4/2000 | Rubin et al. ............. 514/327 |
| 6,071,928 A | 6/2000 | Curtis et al. ............. 514/278 |
| 6,331,536 B1 * | 12/2001 | Radulovacki et al. .. 514/214.02 |

FOREIGN PATENT DOCUMENTS

| | | |
|---|---|---|
| EP | 0 052 492 | 5/1982 |
| EP | 0 100 569 A | 2/1984 |
| EP | 0 201 165 A | 11/1986 |
| EP | 0 411 900 A2 | 2/1991 |
| GB | 2 153 821 A | 8/1985 |
| WO | WO 91 02524 A | 3/1991 |
| WO | WO 91 07175 A | 5/1991 |
| WO | WO 93 00075 A | 1/1993 |
| WO | WO 99/43319 | 9/1999 |

OTHER PUBLICATIONS

Stedman's Medical Dictionary 27$^{th}$ Edition.*
Stedman'Medical Dictionary, 26$^{th}$ Edition, 1995, p. 114.
Phillis, J. W., "Monoamines in the Central Nervous System," The Pharmacology of Synapses, 1970, Monograph, p. 43.
Frazer, A., et al., Annual Rev. of Pharmacology and Therapeutics, 1990, vol. 30, pp. 307–348.
Naylor, R. J., et al.,Euro. J. Anaesth., 1976, vol. 9, pp. 3–10.
Desai, K. M., et al., Br. J. Pharmacol., 1994, vol. 111, pp. 346–350.
Fozard, J. H., et al., Br. J. Pharmacol., 1976, vol. 57, pp. 115–125.
Kim, M. Y., et al., Heterocycles, 1997, vol. 45(10), pp. 2041–2043.
Lochmuller, C. H., et al., J. Chromatogr., 1975, vol. 113(3), pp. 283–302.
Ebert, W. R., Pharm. Tech., 1977, vol. 1(5), pp. 44–50.
Burstein, E. S., et al., J. Biol. Chem., 1995, vol. 270, pp. 3141–3146.
Messier, T. L., et al., Pharmacol. Toxicol., 1995, vol. 75(5), pp. 308–311.
Bradley, P. B., et al., Neuropharmacology, 1986, vol. 25, pp. 563–576.
Dumuis, A., et al., N. S. Arch. Pharmacol., 1989, vol. 340, pp. 403–410.
Miyata, K., et al., J. Pharmacol. Exp. Ther., 1991, vol. 259, pp. 815–819.

(List continued on next page.)

Primary Examiner—Thurman K. Page
Assistant Examiner—Humera N. Sheikh
(74) Attorney, Agent, or Firm—Pennie & Edmonds LLP

(57) ABSTRACT

Methods for the treatment, management, or prevention of apnea and apnea disorders, or symptoms thereof, using a therapeutically effective amount of substantially optically pure R(+) ondansetron, or a pharmaceutically acceptable salt thereof, substantially free of its S(−) stereoisomer.

16 Claims, No Drawings

OTHER PUBLICATIONS

Cohen, M. L., et al., *J. Pharmacol. Exp. Ther.*, 1989, vol. 248, pp. 197–201.

Berkow, R. et al. *The Merck Manual*, 1997, pp. 154–155, 304–305, 1205–1206.

Eliel, E. *Stereochemistry of Carbon Compounds*, 1962, pp. xi–xv.

Ariens, E.J., "Stereoselectivity in Pharmacodynamics and Pharmacokinetics," Schweiz. Med. Wocehnshr., vol. 120, No. 5, pp. 131–134, Feb. 3, 1990.

Ariens, E.J., "Racemic Therapeutics—Ethical and Regulatory Aspects," Eur. J. Clini. Pharmacol., vol. 41, No. 2, pp. 89–93, 1991.

Ariens, E.J., "Racemische Therapeutica Probleemmiddelen," Pharmaceutisch Weekblad, vol. 125, No. 2, pp. 552–554, Jun. 1, 1990 (Abstract).

Butler, A. et al., "Pharmacological Properties of GR38032F, A Novel Antagonist at 5–HT3 Receptors," Br. J. Pharmacol., vol. 94, pp. 397–412, Jun. 1, 1990.

Butler, A., "The Pharmacological Characterization of 5–HT3 Receptors in Three Isolated Preparations Derived From Guinea–Pig Tissues," Br. J. Pharmacol., vol. 101, pp. 591–598, 1990.

De Mulder, P.H.M. et al., "Ondansetron Compared with High–Dose Metoclopramide in Prophylaxis of Acute and Delayed Cisplatin–Induced Nausea and Vomiting," Annals of Internal Medicine, vol. 113, No. 11, pp. 834–840, Dec. 1, 1990. (Abstract).

Graves, T., "Chemotherapy–induced nausea and vomiting: Treatment options," Hosp. Formul., vol. 26, pp. 474–476, 478–480, 485, 488, Jun. 1991. (Abstract).

Hibert, M.F. et al., "Conformation–Activity Relationship Study of 5–HT3 Receptor Antagonists and a Definition of a Model for This Receptor Site," J. Med. Chem. vol. 33, No. 6, pp. 1594–1600, 1900.

Kusnierczyk, H. et al., "Antitumor Activity of Optical Isomers of Cyclophosphamide, Ifosfamide and Trofosfamide as Compared to Clinically Used Racemats," Journal of Immunopharmacology, vol. 8, No. 4, pp. 455–480, 1986. (Abstract).

Nukariya, N. et al., "Examination of anti–emetic effect, safety and usefulness of single oral dose of ondansetron tablet in nausea and emesis induced by anti–cancer drugs–dose–finding study of ondansetron tablet in patients receiving non–platinum anti–cancer drugs." Gan To Kagaku Ryoho, vol. 19, mo. 9, pp. 1347–1357, Aug. 1992. (Abstract).

Nukariya et al., "Examination of anti–emetic effect and safety of multiple intravenous doses of ondansetron in patients receiving nonplatinum anti–cancer drugs," Gan go Kagaku Ryoho, vol. 19, No. 9, pp. 1375–1385, Aug. 1992. (Abstract).

Pinkerton, C.R. et al., "5–HT3 antagonist ondansetron—an effective outpatient antiemetic in cancer treatment," Arch. Dis. Child., vol. 65, No. 8, pp. 822–825, Aug. 1990. (Abstract).

Stevens, R.F., "The Role of Ondansetron in Paediatric Patients: A Review of Three Studies," Eur. J. Cancer, vol. 27, No. Suppl. 1, pp. S20–S22, 1991. (Abstract).

Testa, B. et al., "Racemates Versus Enantiomers in Drug Development: Dogmatism or Pragmatism?" Chirality, vol. 2, pp. 129–133, 1990.

Tonato, M., "Ondansetron Plus Dexamethasone: An Effective Combination in High–dose Cisplatin Therapy," Eur. J. Cancer, vol. 27, No. Suppl 1, pp. S12–S14, 1991. (Abstract).

M. Radulovacki et al., *Serotonin 5–HT3–Receptor Antagonist GR 38023F Suppresses Sleep Apneas in Rats, Sleep*, vol. 21, No. 2, Mar. 15, 1998, pp. 131–136, Allen Press, Lawrence, KA.

M. Yoshioka, et al., *Pharmacological Characterization of 5–Hydroxytryptamine–Induced Apnea in the Rat, J. of Pharmacology and Experimental Therapeutics*, vol. 290, No. 2, 1992, pp. 917–924.

Y. Goda, et al., *The Role of 5–HT3 Receptor Mediated Mechanisms on 5HT–3 Induced Apnea in Anesthetized Rats, European Journal of Pharmacology*, vol. 183, No. 3, 1990, pp. 705–706.

\* cited by examiner

METHODS FOR TREATING APNEA AND APNEA DISORDERS USING OPTICALLY PURE R(+) ONDANSETRON

This is a continuation of application Ser. No. 09/515,407, filed Feb. 29, 2000 which claims the benefit of provisional application No. 60/122,274, filed Mar. 1, 1999.

1. FIELD OF THE INVENTION

The invention relates to methods of treatment, management, or prevention of apnea, apnea disorders, or symptoms thereof.

2. BACKGROUND OF THE INVENTION

Apnea is defined in *Stedman's Medical Dictionary*, 26th Edition, Williams and Wilkins (1995), as the absence of breathing. There are a number of disorders associated with apnea, which are characterized by interrupted breathing in which a person stops breathing long enough to decrease the amount of oxygen and increase the amount of carbon dioxide in the blood and brain. Each type of apnea involves the absence of airflow at the nose or the mouth, typically for at least 10 seconds.

Various apnea disorders exist, including: central apnea, which results from medullary depression and inhibits respiratory movement; deglutition apnea, which is the inhibition of breathing during swallowing; obstructive or peripheral apnea, which is either a result of obstruction of air passages or inadequate respiratory muscle activity; sleep apnea, which is central and/or obstructive apnea during sleep; and sleep induced apnea, which results from failure of the respiratory center to stimulate adequate respiration during sleep.

Obstructive apneas usually occur in obese men and are much less common in women. The obesity, perhaps in combination with aging body tissues and other factors, leads to narrowing of the upper airways. Tobacco smoking, excessive alcohol use, and lung diseases, such as emphysema, increase the risk of developing obstructive apneas.

For those suffering from sleep apnea, quitting smoking, avoiding excessive use of alcohol, and losing weight are commonly the first behavioral steps for treating the disorder. In order to inhibit or avoid apnea, heavy snorers and people who often choke in their sleep should not take tranquilizers, sleep aids, and other sedating drugs.

Sleep apnea is one of the most common forms of apnea. Rarely, a person who has severe sleep apnea needs a tracheostomy, as surgical procedure that creates a permanent opening into the windpipe through the neck. Sometimes other surgical procedures are performed to widen the upper airway and alleviate the problem. However, such extreme measures are seldom needed and never desired.

Apnea can also be treated by non-invasive means, such as therapeutic drugs, by administering to a patient a therapeutic agent. U.S. Pat. No. 5,075,290 discloses the medical treatment of obstructive sleep apnea and associated symptoms, such as snoring, by the administration of the nucleoside uptake blocker, dipyridamole, during sleep. U.S. Pat. Nos. 5,502,067 and 5,407,953 disclose a method of treating sleep apnea, hyponea and snoring in a human patient by administering a pilocarpine compound. U.S. Pat. No. 5,422,374 discloses a method of treating sleep apnea by the administration of ubidecarenone to a patient. U.S. Pat. No. 5,356,934 discloses a method of employing (R)-fluoxetine to treat sleep apnea.

Ondansetron, which is available commercially only as a 1:1 racemic mixture of its R and S enantiomers, is a well known anti-emetic agent. Commonly administered as a hydrochloride salt, it is an antagonist of the 5-hydroxytryptamine (5-HT or serotonin) receptor, subtype 5-$HT_3$. The role of serotonin has been broadly implicated in a variety of conditions for many years. See, e.g., Phillis, J. W., *The Pharmacology of Synapses*, Pergamon Press, Monograph, 43 (1970); Frazer, A. et al., *Annual Rev. of Pharmacology and Therapeutics*, 30:307–348 (1990). Research has focused on locating the production and storage sites of serotonin, as well as on the location of serotonin receptors in the human body, to determine the connection between these sites and various disease states or conditions.

Most research regarding the compound ondansetron has been directed to understanding its ability to reduce chemotherapy- and radiotherapy-induced emesis. See, e.g., Naylor, R. J. et al., *Euro. J. Anaesth.*, 9:3–10 (1992). The usefulness of racemic ondansetron in this regard is quite clear. For example, its use as an antiemetic by either intravenous or oral routes is disclosed in U.S. Pat. Nos. 4,753,789 and 4,929,632. Recently, it has been reported that the optically pure R(+) stereoisomer of ondansetron is also useful for treating emesis. Specifically, U.S. Pat. No. 5,712,302 discloses methods and compositions utilizing R(+) ondansetron for the treatment of nausea and vomiting associated with chemotherapy and radiation therapy.

Although the ability of both racemic and optically pure ondansetron to antagonize retching and vomiting has encouraged research, many questions concerning the pharmacology of the compound remain unanswered. Kesai, K. M., *Br. J. Pharmacol.*, 111:346–350 (1994). Current understanding is based upon the fact that racemic ondansetron is an antagonist of serotonin 5-$HT_3$ receptors. Serotonin is a neurotransmitter that has powerful vasoconstrictor properties, and is capable of depolarizing the sympathetic nerve fibers to the heart. Fozard, J. H. et al., *Br. J. Pharmacol.*, 57:115–125 (1976). Along with other types of 5-HT receptors found in mammals, 5-$HT_3$ receptors have been located in the mammalian hind-brain, peripherally on the vagal nerve, and on neuronal elements in the gastrointestinal tract. It has been theorized that physical disruptions of the gastrointestinal tract can somehow cause the release of humoral substances including serotonin, which stimulate receptors on the vagal nerves and which in turn trigger the emetic reflex. Naylor, R. J. et al., *Euro. J. Anaesth.*, 9:3–10 (1992).

It is desirable to provide methods of treating, preventing, or managing apnea and apnea disorders, including sleep apnea, or symptoms thereof.

3. SUMMARY OF THE INVENTION

The present invention encompasses the use of optically pure R(+) ondansetron, or a pharmaceutically acceptable salt thereof, substantially free of its S(−) stereoisomer, in preventing, treating or managing apnea or apnea disorders, or symptoms thereof in a patient. The invention also encompasses the use of optically pure R(+) ondansetron, or a pharmaceutically acceptable salt thereof, substantially free of its S(−) stereoisomer, in treating these disorders while avoiding or decreasing adverse effects including, but not limited to, headache, constipation and increases in transaminase levels which are associated with the racemic mixture of ondansetron. It should be understood that the invention encompasses any combination of preventing, treating, or managing apnea or apnea disorders.

This invention also encompasses compositions adapted for the treatment of a patient suffering from apnea or related diseases, or symptoms thereof, which comprises a therapeutically effective amount of R(+) ondansetron, or a pharmaceutically acceptable salt thereof, substantially free of its S(−) stereoisomer; and a pharmaceutically acceptable carrier. The invention encompasses single unit dosage forms that comprise from about 0.001 mg to about 35 mg of optically pure R(+) ondansetron, or a pharmaceutically acceptable salt thereof, substantially free of its S(−) stereoisomer, i.e., an amount particularly suitable for the prevention, treatment, or management of apnea and apnea disorders. In one embodiment, the pharmaceutical compositions of the present invention encompass a solid unit dosage form comprising from about 10 mg to about 35 mg of optically pure R(+) ondansetron, or a pharmaceutically acceptable salt thereof, substantially free of its S(−) stereoisomer; and a pharmaceutically acceptable carrier.

4. DETAILED DESCRIPTION OF THE INVENTION

The present invention encompasses the use of optically pure R(+) ondansetron, or a pharmaceutically acceptable salt thereof, substantially free of its S(−) stereoisomer, in preventing, treating or managing apnea or apnea disorders, or symptoms thereof in a patient. Apnea or apnea disorders treated include, but are not limited to, central apnea, deglutition apnea, obstructive or peripheral apnea, sleep apnea, and sleep induced apnea, as well as any combination thereof.

The invention also encompasses use of optically pure R(+) ondansetron, or a pharmaceutically acceptable salt thereof, substantially free of its S(−) stereoisomer, for the treatment, prevention, or management of apnea or apnea disorders, or symptoms thereof, preferably while causing fewer adverse effects than racemic ondansetron.

The methods of the present invention are particularly useful for the treatment of obese men. In a preferred embodiment, the methods are directed to the treatment of obstructive apnea in obese men. It should be recognized that the methods can be used to treat males and females, including children and adults, notwithstanding the preferences mentioned above.

Further, the invention includes the use of R(+) ondansetron, or a pharmaceutically acceptable salt thereof, substantially free of its S(−) stereoisomer, in combination with one or more other therapeutic agents for the treatment of apnea, including, but not limited to, fluoxetine or the R or S stereoisomer thereof; norcisapride or the (+) or (−) stereoisomer thereof; ubidecarenone; dipyramole; pilocarpine or a stereoisomer thereof; primidone or the R or S stereoisomer thereof; orphenadrine citrate; and the like. The administration of R(+) ondansetron, or a pharmaceutically acceptable salt thereof, substantially free of its S(−) stereoisomer, in combination with other therapeutic agents for the treatment of apnea, in the methods of the present invention may be made either concurrently or sequentially, i.e., R(+) ondansetron and at least one other therapeutic agents for the treatment of apnea may be administered as a combination, concurrently but separately, or by the sequential administration. The compositions administered in each of these methods may be concurrent, sequential, or in any combination of concurrent or sequential.

As used herein, the terms "adverse effects" and "adverse side effects" each include, but are not limited to, cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to, ventricular tachyarrhythmias, torsades de pointes, and ventricular fibrillation.

The term "racemic" as used herein means a mixture of the (+) and (−) enantiomers of a compound wherein the (+) and (−) enantiomers are present in approximately a 1:1 ratio.

The terms "substantially optically pure," "optically pure," and "optically pure enantiomers," as used herein, mean that the composition contains greater than about 90% of the desired enantiomer by weight, preferably greater than about 95% of the desired enantiomer by weight, and more preferably greater than about 99% of the desired enantiomer by weight, based upon the total weight of ondansetron. The term "substantially free," as used herein, means less than about 10 weight percent, preferably less than about 5 weight percent, and more preferably less than about 1 weight percent of S(−) ondansetron is present according to the invention.

The phrases "apnea" and "apnea disorders," as used herein, are defined as breathing interruption disorders including, but not limited to, central apnea, deglutition apnea, obstructive or peripheral apnea, sleep apnea, and sleep induced apnea, as well as any combination thereof.

The phrase "therapeutically effective amount of R(+) ondansetron," as used herein, means that amount of substantially optically pure R(+) ondansetron, or a pharmaceutically acceptable salt thereof, substantially free of its S(−) stereoisomer, which, alone or in combination with other drugs, provides a therapeutic benefit in the treatment, management, or prevention of apnea or apnea disorders, or one or more symptoms thereof.

The preparation of the mixture of enantiomers, (e.g., racemic mixture) of ondansetron is well known to those of ordinary skill in the art, particularly in view of U.S. Pat. No. 4,695,578, which is hereby incorporated herein by express reference thereto, and Kim, M. Y et al., *Heterocycles*, Vol. 45, No. 10, Pg. 2041–2043, 1997. The R(+) isomer of ondansetron may be obtained by resolution of the mixture of enantiomers of ondansetron using conventional means, including, but not limited to, an optically active resolving acid. This synthesis is also known to those of ordinary skill in the art, particularly from "Stereochemistry of Carbon Compounds", by E. L. Eliel (McGraw Hill 1962) and Lochmuller C. H. et al., *J. Chromatogr.*, 1975, Vol. 113, No. 3, Pg. 283–302.

The magnitude of a prophylactic or therapeutic dose of R(+) ondansetron, or a pharmaceutically acceptable salt thereof, substantially free of its S(−) stereoisomer, in the acute or chronic management of diseases will vary with the severity of the condition to be treated, and the route of administration. For example, oral, mucosal (including rectal), parenteral (including subcutaneous, intramuscular, bolus injection, and intravenous), sublingual, transdermal, nasal, buccal, and like may be employed. Dosage forms include tablets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those skilled in the art with due consideration of such factors.

Any suitable route of administration may be employed, however, for providing the patient with an effective dosage of R(+) ondansetron. The most suitable route in any given case will depend on the nature and severity of the condition being treated. For example, oral, mucosal (including rectal), parenteral (including intravenous, intramuscular, subcutaneous, bolus injection), transdermal, sublingual, nasal, buccal, and the like may be employed. Dosage forms include tablets, troches, lozenges, suppositories, dispersions, suspensions, solutions, capsules, patches, and the like. The most preferred route of administration for the present invention is oral. The oral dosage forms may be conveniently presented in unit dosage form and prepared by any of the methods well know in the art of pharmacy.

The pharmaceutical compositions of the present invention comprise R(+) ondansetron, or a pharmaceutically acceptable salt thereof, substantially free of its S(−) stereoisomer, as an active ingredient, and may also contain a pharmaceutically acceptable carrier, and optionally, other therapeutic ingredients. As used herein, the term "pharmaceutically acceptable salt" refers to a salt prepared from pharmaceutically acceptable non-toxic acids including inorganic acids, organic acids, solvates, hydrates, or clatherates thereof Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, paratoluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Particularly preferred acids are hydrobromic, hydrochloric, phosphoric, and sulfuric acids.

In the case where an oral composition is employed, a suitable dosage range for use is, e.g., from about 0.001 mg to about 35 mg total daily dose, administered as a single dose or as equally divided doses up to four times a day. Preferably, the dose range is from about 0.5 mg to about 30 mg per day, administered as a single dose or equally divided doses, from two to four times a day, and most preferably from about 1 mg to about 25 mg per day, typically administered as a single dose or equally divided doses, two to four times a day. Patients may be upwardly titrated within this dose range to enable the satisfactory control of symptoms.

In the case where an intravenous injection or infusion composition is employed, a suitable dosage range for use is, e.g., from about 0.001 mg to about 35 mg total daily dose, preferably from about 0.5 mg to about 30 mg, more preferably from about 1 mg to about 25 mg, presented as a slow intravenous injection of about 0.001 mg to about 11 mg over 15 to 30 minutes, followed by an intravenous infusion of about 0.5 mg to about 1 mg/hour for up to 24 hours. These regimens may be followed by oral doses of from about 1.5 mg to about 8 mg about every eight hours for periods up to five days.

In practical use, R(+) ondansetron, or a pharmaceutically acceptable salt thereof, substantially free of its S(−) stereoisomer, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous or intramuscular injections, or infusions). In preparing the compositions for oral dosage form, any of the usual pharmaceutically acceptable carriers known to those of ordinary skill in the art may be employed, e.g., water, glycols, oils, alcohols, flavoring agents, preservatives, coloring agents, and the like in the case of oral liquid preparations, e.g., suspensions, solutions, and elixirs; or aerosols; or in the case of solid preparations, including, but not limited to, starches, sugars, microcrystalline cellulose, diluents, granulating agents, lubricants, binders, disintegrating agents, and the like in the case of oral solid preparations, e.g., powders, capsules, troches, cachets, and tablets, with the solid oral preparations being preferred over the liquid preparations. The most preferred solid oral preparation is tablets.

Because of their ease of administration, tablets and capsules represent the most advantageous oral dosage unit form, in which case solid pharmaceutical carriers are employed. If desired, tablets may be coated by standard aqueous or non-aqueous techniques, and may be formulated for controlled-release using techniques well known to those of ordinary skill in the art.

In addition to the common dosage forms set out above, the compounds of the present invention may also be administered by controlled release means or delivery devices that are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations known to those of ordinary skill in the art, including those described herein, may be readily selected for use with the R(+) ondansetron compositions of the invention. Thus, single unit dosage forms suitable for oral administration, such as tablets, capsules, gelcaps, caplets and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradual and continual release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of the active ingredient may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., R(+) ondansetron) in the pharmaceutical composition.

Another preferred route of administration is transdermal delivery, for example, via an abdominal skin patch.

Pharmaceutical compositions of the present invention suitable for oral administration may be presented as discrete units, including, but not limited to, capsules, cachets, troches, caplets, gelcaps, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association, the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine, the active ingredient in a free-flowing form, including, but not limited to, powder or granules, optionally mixed with a pharmaceutically acceptable carrier, which may comprise one or more of a lubricant, inert diluent, surface active or dispersing agent, or the like. Molded tablets may be made by molding in a suitable machine, a mixture of the powdered compound, moistened with an inert liquid diluent. Desirably, each tablet, cachet, or capsule contains from about 0.001 mg to about 35 mg of the active ingredient of the active ingredient. However, the amount of active ingredient found in the composition may vary depending on the amount of active ingredient to be administered to the patient.

Optically pure R(+) ondansetron for use in the present invention may be formulated as a pharmaceutical composition in a soft elastic gelatin capsule unit dosage form by using conventional methods well known in the art. See, e.g., Ebert, *Pharm. Tech,* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, including, but not limited to, methyl- and propylparabens and sorbic acid, to prevent the growth of fungi. The active ingredient may be dissolved or suspended in a liquid vehicle or carrier, including, but not limited to, vegetable or mineral oils, glycols, including, but not limited to, polyethylene glycol and propylene glycol, triglycerides, surfactants, including, but not limited to, polysorbates, or a combination thereof.

The invention is further defined by reference to the following examples describing in detail, the preparation of the compound, and the compositions of the present invention. It will be apparent to those skilled in the art, that many modifications, both to materials and methods, may be practiced without departing from the purpose and interest of this invention.

5. EXAMPLES

5.1. Example 1: Bioavailability

A single dose of test substance or vehicle is administered to male beagle dogs either intravenously as a bolus over one minute using a 23 gauge butterfly needle into the saphenous vein, or as a single dose via oral gavage. 2.0 mL of whole blood is collected from each dog prior to and at intervals of 0.083, 0.25, 0.5, 1, 2, 3, 4, 6, 9, 12, and 24 hours following the intravenous or oral administration of an optical isomer or racemic mixture of ondansetron. The dogs are placed in sling-restraint prior to administration of test substance and are transferred to metabolic cages following collection of the 0.083 hour blood sample. All blood samples are collected from an angiocatheter placed in a cephalic vein on the morning of the experiment.

The blood is drawn into a 3 cc syringe. The first 1.0–2.0 mL of blood is discarded. The next 2.0 mL of whole blood is quickly transferred to a heparinized tube. The heparinized tubes are kept on ice until the blood is added. After adding the blood to the tube, the contents of the tube are mixed and centrifuged to obtain plasma. The plasma is carefully decanted and transferred to a test tube labeled with: the animal number, the dose of test substance administered, the route of administration, the date of administration, and the time of blood collection. The tubes are stored at −20° C. until analysis.

Analysis of the concentration of the optical isomers or racemate of ondansetron in each plasma sample is determined using high performance liquid chromatography. For each test substance the plasma concentration with respect to sample time is plotted for both routes of administration. The oral bioavailability of each test substance is determined by comparing the $C_{max}$ and AUC for the oral route of administration versus those for the intravenous route. The $t_{1/2}$ for each test substance by both routes is calculated as an indicator of duration of action.

5.2 Example 2

Receptor Activity

5-HT$_{1A}$ Receptor Activity

Receptor selection and amplification technology (R-SAT) is used (Receptor Technologies Inc., Winooski, Vt.) to determine potential agonist and/or antagonist activity of racemic ondansetron, R(+) ondansetron, and S(−) ondansetron on cloned human serotonin 5-HT$_{1A}$ receptor subtypes expressed in NIH 3T3 cells, such as in Burstein et al., *J. Biol Chem.,* 270:3141–3146 (1995); and Messier et al., *Pharmacol. Toxicol.,* 76(5):308–311 (1995).

The assay involves co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells are incubated, plated, and then transfected using human 5-HT$_{1A}$ serotonin receptors, pSV-β-galactosidase, and salmon sperm DNA. The medium is changed one day later, and after 2 days, aliquots of the trypsinized cells are placed in wells of a 96 well plate. After five days in culture in the presence of the ligands, the levels of β-galactosidase are measured. The cells are then rinsed and incubated with the substrate, o-nitrophenyl β-D-galactopyranoside. After 16 hours, the plates are read at 405 nm on a plate-reader. Each compound is tested for activity in triplicate at seven different concentrations (10, 2.5, 0.625, 0.156, 0.039, 0.0098, and 0.0024 nM).

5-HT$_2$ Receptor Activity

Receptor selection and amplification technology (R-SAT) is used (Receptor Technologies Inc., Winooski, Vt.) to determine potential agonist and/or antagonist activity of racemic ondansetron, R(+) ondansetron, and S(−) ondansetron on cloned human serotonin 5-HT$_2$ receptor subtypes expressed in NIH 3T3 cells, such as in Burstein et al., *J. Biol Chem.*, 270:3141–3146 (1995); and Messier et al., *Pharmacol. Toxicol.*, 76(5):308–311 (1995).

The assay involves co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells are incubated, plated, and then transfected using human 5-HT$_2$ serotonin receptors, pSV-β-galactosidase, and salmon sperm DNA. The medium is changed one day later, and after 2 days, aliquots of the trypsinized cells are placed in wells of a 96 well plate. After five days in culture in the presence of the ligands, the levels of β-galactosidase are measured. The cells are then rinsed and incubated with the substrate, o-nitrophenyl β-D-galactopyranoside. After 16 hours, the plates are read at 405 nm on a plate-reader. Each compound is tested for activity in triplicate at seven different concentrations (10, 2.5, 0.625, 0.156, 0.039, 0.0098, and 0.0024 nM).

5.3. Example 3

Receptor Binding

5-HT$_3$ Receptor

A pharmacological study may be conducted to determine the relative potency and specificity of optically pure R(+) ondansetron and racemic ondansetron as competitive antagonists at serotonin receptor subtype 5-HT$_3$ present in gastrointestinal, brain, and other tissues.

Optically pure and racemic compounds may be evaluated as a function of their molar concentration, for their relative abilities to inhibit the binding of $^3$H-5-HT in such selected preparations as nerves of guinea pig ileum and preparations of brain tissue from several species including rats and humans. The availability of $^3$H-5-HT as a radioligand with relatively high specific activity, the development of other selective 5-HT$_3$ antagonists, and the additional agonist, 2-methyl-5-hydroxy-tryptamine (2-methyl-5-HT) provide the pharmacologic tools for the characterization of the 5-HT$_3$ receptor, and the evaluation of R(+) ondansetron and racemic ondansetron. See Frazer, A., et al., *Annu. Rev. Pharmacol. Toxicol.* 30:307–348 (1990) and Bradley, P. B. et al., *Neuropharmacology* 25:563–576 (1986).

For example, racemic ondansetron, and its R(+)- and S(−)-stereoisomers can be tested for binding to 5-HT$_3$ receptor subtypes derived from N1E-115 cells using a radio-ligand binding procedure. For example, following incubation with the appropriate ligands, cell preparations are rapidly filtered under vacuum through GF/B glass fiber filters and washed with ice-cold buffer using a Brandel or Packard cell harvester. Bound radioactivity is determined with a liquid scintillation counter (e.g., LS 6000, Beckman) using a liquid scintillation cocktail (e.g., Formula 989).

Specific radioligand binding to the receptor is defined as the difference between total binding and nonspecific binding determined in the presence of an excess of unlabeled ligand. Results are expressed as a percent inhibition of specific binding obtained in the presence of the compounds. IC$_{50}$ are determined using concentrations ranging from $3 \times 10^{-10}$ M to $10^{-5}$ M to obtain full competition curves and are calculated by non-linear regression analysis.

5-HT$_4$ Receptor

For example, racemic ondansetron and its R(+)- and S(−)-stereoisomers are tested for binding to 5-HT$_4$ receptor subtypes derived from guinea-pig striata using a radio ligand binding procedure. For example, following incubation with the appropriate ligands, cell preparations are rapidly filtered under vacuum through GF/B glass fiber filters and washed with ice-cold buffer using a Brandel or Packard cell harvester. Bound radioactivity is determined with a liquid scintillation counter (e.g., LS 6000, Beckman) using a liquid scintillation cocktail (e.g., Formula 989).

Specific radioligand binding to the receptor is defined as the difference between total binding and nonspecific binding determined in the presence of an excess of unlabeled ligand. Results are expressed as a percent inhibition of specific binding obtained in the presence of the compounds. IC$_{50}$ are determined using concentrations ranging from $3 \times 10^{-10}$ M to $10^{-5}$ M to obtain full competition curves and are calculated by non-linear regression analysis.

Agonist activity at 5-HT$_4$ receptor sites may also be assessed using an assay based on the ability of active compounds to increase cyclic AMP production in mouse embryo colloculi neurones grown in tissue culture, such as in Dumuis et al., *N. S. Arch. Pharmacol.*, 340:403–410 (1989).

5.4. Example 4

In Vivo 5-HT Antagonist Activity

An investigation of the serotonin (5-HT) antagonist activity of the racemic ondansetron and the R(+)- and S(−)-enanatiomers of ondansetron in anestetized rats is conducted using a model similar to Cohen et al., *Pharmacol. Exp. Ther.*, 248:197 (1989) and Miyata et al., *J. Pharmacol. Exp. Ther.*, 259:815 (1991) (the Bezold-Jarish test). This investigation is used to determine the in vivo 5-HT antagonist activity of the test compounds.

5.5. Example 5

Electrophysiological Effects of R-Ondansetron in Conscious Dogs

An investigation was conducted to determine the effect of racemic ondansetron and the R(+)- and S(−)-enanatiomers of ondansetron in causing cardiac arrhythmias (cardiotoxicity) resulting from a lengthening of the cardiac action potential.

R(+)-ondansetron, S(−) ondansetron, and racemic ondansetron were administered at 0.0, 1.0, 2.0, and 4.0 mg/kg in 30 minute intervals in a rising, cumulative-dose fashion to four mongrel dogs. The dogs had at least one week to acclimate between treatments. The order of administration was randomized to ensure that each dog received only one treatment. Heart rate, QT interval, QTc interval, PR interval, and QRS interval were measured prior to, and at hourly intervals, following the administration of R(+)-ondansetron, S(−) ondansetron, or racemic ondansetron. These measurements were used to assess the potential for test compounds to produce undesirable EKG effects and are set forth in TABLE 1 below.

TABLE I

Effects of R(+)-, S(–)-, and R,S-Ondansetron on QTc Interval (sec.) in Anesthetized Dogs

|  | 0 mg/kg | 1.0 mg/kg | 2.0 mg/kg | 4.0 mg/kg |
|---|---|---|---|---|
| R(+)-Ondansetron | 0.36 ± 0.00 | 0.39 ± 0.01 | 0.40 ± 0.01 | 0.41 ± 0.02 |
| S(–)-Ondansetron | 0.37 ± 0.02 | 0.43 ± 0.02 | 0.44 ± 0.04 | 0.44 ± 0.03 |
| R,S-Ondansetron | 0.36 ± 0.01 | 0.41 ± 0.01 | 0.45 ± 0.01 | 0.47 ± 0.01 |

N = 4 except for S(–) ondansetron, where N = 3 in the highest dose group*
*2 dogs died in the S(–) ondansetron group. One dog was substituted; the other dog died after the 4 mg/kg dose and was not substituted.

These results demonstrate that among the animals tested, the QTc interval, which is the EKG representation of the cardiac action potential corrected for heart rate, was most prolonged among animals receiving S(–) ondansetron and racemic ondansetron and shortest among animals receiving R(+) ondansetron. Prolongation of QTc interval can cause fatal cardiac arrhythmias of a type called "torsade des pointes." Significantly, two of the four dogs receiving S(–) ondansetron died during or shortly after the experiment, whereas all the dogs receiving the R(+)-stereoisomer or the racemate survived. Based on these data, R(+) ondansetron was thus shown to have less cardiotoxicity than either S(–) ondansetron or racemic ondansetron.

5.6. Example 6

ORAL FORMULATION

| Tablet: | Quantity per Tablet in mg | | |
|---|---|---|---|
| Formula | A | B | C |
| Active Ingredient R(+) ondansetron | 1.0 | 5.0 | 10.0 |
| Lactose BP | 152.5 | 148.5 | 143.5 |
| Starch BP | 30.0 | 30.0 | 30.0 |
| Pregelatinized Maize Starch BP | 15.0 | 15.0 | 15.0 |
| Magnesium Stearate BP | 1.5 | 1.5 | 1.5 |
| Compression Weight | 200.0 | 200.0 | 200.0 |

The active ingredient is sieved through a suitable sieve and blended with lactose, starch, and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to pharmaceutically acceptable excipients or the compression weight and using punches to suit.

5.7. Example 7

ORAL FORMULATION

| Capsules: | mg/capsule | | |
|---|---|---|---|
| Formula | A | B | C |
| Active Ingredient R(+) ondansetron | 1.0 | 5.0 | 10.0 |
| Starch 1500 | 98.0 | 94.0 | 89.0 |
| Magnesium Stearate BP | 1.0 | 1.0 | 1.0 |
| Compression Weight | 100.0 | 100.0 | 100.0 |

The active ingredient is sieved and blended with the excipients. The mix is filled into size No. 2 hard gelatin capsules using suitable machinery. Other doses may be prepared by altering the fill weight and if necessary changing the capsule size to suit.

5.8. Example 8

INTRAVENOUS FORMULATION

| Formula | µg/ml |
|---|---|
| Active Ingredient R(+) ondansetron | 400 |
| Dilute Hydrochloric Acid BP | to pH 3.5 |
| Sodium Chloride Injection BP | 1 mL |

The active ingredient is dissolved in dilute hydrochloric acid BP to form a solution having a concentration of 400 µg/mL R(+) ondansetron. The solution is then mixed with sodium chloride injection BP prior to use.

While the present invention has been described with respect to particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating apnea or an apnea disorder in a patient which comprises administering a therapeutically effective amount of R(+) ondansetron, or a pharmaceutically acceptable salt thereof, substantially free of its S(–) stereoisomer, and a therapeutically effective amount of at least one other therapeutic agent selected from fluoxetine or the R or S stereoisomer thereof, norcisapride or the (+) or (–) stereoisomer thereof, ubidecarenone, dipyramole, pilocarpine or a stereoisomer thereof, primidone or the R or S stereoisomer thereof, or orphenadrine citrate.

2. The method according to claim 1, wherein the apnea or apnea disorder being treated is selected from the group consisting of central apnea, deglutition apnea, obstructive apnea, sleep apnea, and sleep induced apnea.

3. The method of claim 1, which comprises administering the R(+) ondansetron and the at least one other therapeutic agent for the treatment of apnea concurrently or sequentially.

4. A method of treating apnea or an apnea disorder in a patient which comprises orally administering a therapeutically effective amount of R(+) ondansetron, or a pharmaceutically acceptable salt thereof, substantially free of its S(−) stereoisomer, and a therapeutically effective amount of at least one other therapeutic agent for the treatment of apnea.

5. The method of claim 4, Wherein R(+) ondansetron is administered as a tablet or a capsule.

6. The method of claim 5, wherein said R(+) ondansetron is administered from one to four times per day.

7. The method according to claim 1, wherein the amount R(+) ondansetron administered is from about 0.001 mg to about 35 mg.

8. A method of treating apnea or an apnea disorder in a patient which comprises parenterally administering a therapeutically effective amount of R(+) ondansetron, or a pharmaceutically acceptable salt thereof, substantially free of its S(−) stereoisomer, and a therapeutically effective amount of at least one other therapeutic agent for the treatment of apnea.

9. The method of claim 8, wherein the R(+) ondansetron is administered parenterally by a slow intravenous injection of about 0.001 mg to 11 mg over 15 to 30 minutes followed by an intravenous infusion of about 0.5 to about 1 mg/hour for up to 24 hours.

10. The method of claim 9, further comprising orally administering R(+) ondansetron in an amount of about 1.5 mg to 8 mg.

11. The method of claim 10, wherein the orally administered R(+) ondansetron is administered about every 8 hours for up to 5 days.

12. The method according to claim 1, wherein the amount of R(+) ondansetron, or a pharmaceutically acceptable salt thereof, is greater than approximately 90% by weight of the total ondansetron.

13. The method according to claim 1, wherein R(+) ondansetron or a pharmaceutically acceptable salt thereof, substantially free of its S(−) stereoisomer, is administered together with a pharmaceutically acceptable carrier.

14. The method according to claim 1, wherein R(+) ondansetron hydrochloride is administered.

15. The method of claim 1, wherein the at least one other therapeutic agent for the treatment of apnea is norcisapride or the (+) or (−) stereoisomer thereof.

16. The method of claim 1, wherein the R(+) ondansetron is administered nasally.

* * * * *